(12) United States Patent
Stepp

(10) Patent No.: US 8,981,138 B2
(45) Date of Patent: Mar. 17, 2015

(54) METHOD FOR PRODUCING AMINOORGANOSILANES

(75) Inventor: Michael Stepp, Ueberackern (AT)

(73) Assignee: Wacker Chemie AG, Munich (DE)

( * ) Notice: Subject to any disclaimer, the term of this patent is extended or adjusted under 35 U.S.C. 154(b) by 336 days.

(21) Appl. No.: 13/375,081

(22) PCT Filed: Jun. 1, 2010

(86) PCT No.: PCT/EP2010/057582
§ 371 (c)(1),
(2), (4) Date: Nov. 29, 2011

(87) PCT Pub. No.: WO2010/139674
PCT Pub. Date: Dec. 9, 2010

(65) Prior Publication Data
US 2012/0071650 A1 Mar. 22, 2012

(30) Foreign Application Priority Data
Jun. 4, 2009 (DE) .......................... 10 2009 026 755

(51) Int. Cl.
*C07F 7/10* (2006.01)
*C07F 7/18* (2006.01)

(52) U.S. Cl.
CPC .................................... *C07F 7/1892* (2013.01)
USPC ............................. 556/413; 556/400; 556/453

(58) Field of Classification Search
USPC .......................................... 556/413, 453, 400
See application file for complete search history.

(56) References Cited

U.S. PATENT DOCUMENTS

| | | | |
|---|---|---|---|
| 3,673,233 A | 6/1972 | Golitz et al. | |
| 5,616,755 A | 4/1997 | Seiler et al. | |
| 6,150,551 A | 11/2000 | Kropfgans et al. | |
| 6,417,381 B1 | 7/2002 | Gedon et al. | |
| 6,452,033 B1 * | 9/2002 | Maki et al. | 556/424 |
| 8,314,263 B2 * | 11/2012 | Ziche et al. | 556/413 |
| 2002/0042491 A1 | 4/2002 | Brader et al. | |
| 2006/0194976 A1 * | 8/2006 | Kornek | 556/424 |
| 2009/0253925 A1 * | 10/2009 | Kornek et al. | 556/413 |
| 2011/0166373 A1 | 7/2011 | Ziche et al. | |

FOREIGN PATENT DOCUMENTS

| | | |
|---|---|---|
| CN | 1347885 A | 5/2002 |
| CN | 1612884 A | 5/2005 |
| DE | 1812564 | 6/1970 |
| DE | 19941283 A1 | 5/2000 |
| DE | 102004060627 A1 | 7/2006 |
| DE | 102007037193 A1 | 2/2009 |
| EP | 0702017 A1 | 3/1996 |
| GB | 686068 | 1/1953 |

OTHER PUBLICATIONS

International Search Report for PCT/EP2010/057582 dated Jul. 15, 2010.

* cited by examiner

*Primary Examiner* — Sudhakar Katakam
*Assistant Examiner* — Pancham Bakshi
(74) *Attorney, Agent, or Firm* — Caesar, Rivise, Bernstein, Cohen & Pokotilow, Ltd.

(57) ABSTRACT

The invention relates to a method (a) for producing aminoorganyltriorganylsilanes of the general formula (1) $R'_{3-n}R^1{}_n Si{-}R^2{-}NR^3R^4$ (1), a method (b) for producing cyclic aminosilanes of the general formula (4), and a method (III) for producing silylorganoamines of the general formula (7) $R^{01}{}_{3-r}R^{11}{}_r Si{-}R^{12}{-}NR^{13}{-}R^{14}{-}SiR^{02}{}_{3-s}R^{15}{}_s$ (7), wherein amines are reacted with halogen organylsilanes, wherein R', $R^1, R^2, R^3, R^4, R, R^5, R^6, R^{01}, R^{02}, R^{11}, R^{12}, R^{13}, R^{14}, R^{15}$, n, and s have the meanings specified in claims 1 to 3, wherein after the reaction, the ammonium halides of the amines produced as by-products are released by adding a base (B) to the reaction mixture, the amines are removed from the reaction mixture by distillation, two liquid phases are formed by further adding base (B) to the reaction mixture, wherein the one phase contains at least 90 wt % of the hydrohalide of the base (B) and said phase is separated.

(4)

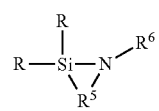

6 Claims, No Drawings

METHOD FOR PRODUCING AMINOORGANOSILANES

BACKGROUND OF THE INVENTION

The invention relates to a method for producing aminoorganosilanes by reacting amines with (haloorganyl)silanes and liberating the by-produced ammonium halide of the amine with a base.

The prior art discloses various methods for producing aminoorganosilanes. The production of amino functional organosilanes is effected predominantly by reacting chlorofunctional organosilanes with very different types of organic amines or ammonia. As a rule, the procedure is such that at least two moles of amine or ammonia are used per mole of chlorofunctional organosilane, so that, in addition to the formation of the aminofunctional organosilane, there is still sufficient amine component available for converting the substituted chlorine into the corresponding amine hydrochloride or ammonium chloride.

In particular, the high availability of (chloroalkyl)-silanes, which are obtainable by means of photochlorination of alkylsilanes or hydrosilylation of corresponding halogen-substituted olefins on Si—H-containing compounds and are used, for example, as intermediates for the synthesis of a multiplicity of organofunctional silanes, is advantageous here.

Furthermore, it is possible in this method to rely not only on ammonia but also on a large number of readily available primary and secondary amines for synthesizing the (N-organylaminoorganyl)- and (N,N-diorganylamino-organyl)triorganylsilanes, which permits a very wide area of use of the method and thereby economical product change on existing industrial manufacturing plants.

GB 686,068 A discloses (amino)-, (N-organylamino)- and (N,N-diorganylaminomethyl)- or (N,N-diorganylaminoethyl)triorganylsilanes. Furthermore, GB 686,068 A describes a method for reacting corresponding (chloromethyl)- or (bromomethyl)triorganosilanes with ammonia, a primary or secondary amine at temperatures of at least 50° C. for the production of said (aminoorganyl)-, (N-organylaminoorganyl)- and (N,N-diorganylaminoorganyl)triorganylsilanes. As a rule, the (chloromethyl)- or (bromomethyl)triorganosilanes are initially introduced into a flask or autoclave, depending on the boiling points of the amine compounds used, and are heated to temperatures above 100° C., preferably 110-130° C. In the case of higher-boiling amines (e.g. cyclohexylamine), the sequence of mixing can be reversed, i.e. the (chloromethyl)- or (bromomethyl)triorganosilanes are added to the heated amine.

According to a method described in DE 1812564 A1, (aminomethyl)silane derivatives are produced by reacting a (chloromethyl)- or (bromomethyl)silane derivative with ammonia or a primary amine. The reaction is effected at temperatures of 80 or 100° C. in a period of 3 or 2 hours, the amine having been completely initially introduced in a molar excess of 1:3.2-6 as early as the beginning of the reaction.

DE 10 2004 060 627 A describes a variation of these methods in which the abovementioned reactions are carried out continuously.

The prior art further discloses methods for reducing halide contents in alkoxysilanes, for example EP 0702017 A discloses those which are based on the precipitation of dissolved amine hydrochloride moieties by addition of alkali metal or alkaline earth metal alcoholate salts. An alternative method which is said to permit reductions of chloride contents in alkoxysilanes by introduction of ammonia is described in DE 19941283 A1.

A disadvantage of all these methods is the fact that (optionally organically substituted) ammonium halides are formed in quantitative amounts as byproducts and have to be separated off as solids. Separating off such large amounts of solid is time-consuming and hence expensive and moreover requires production plants which have appropriate apparatuses, for example powerful and therefore expensive centrifuges. However, this is not the case in many plants—in particular in most multipurpose plants as are typically used for producing fine chemicals.

Here, for example, U.S. Pat. No. 6,452,033 A describes the production of aminoethylaminoorganyltriorganylsilanes by reacting the corresponding chlorofunctional organosilanes with ethylenediamine, the above-mentioned phase separation for separating the hydrochlorides being used in various ways. However, a disadvantage of this method is the fact that it is limited to silanes which have an ethylenediamine unit.

DE 102007037193 A describes a process for production of aminoorganyltriorganylsilanes which comprises a first step of reacting a halo(organyl)silane with an amine to form an amino-functional silane (and by-produce the amine hydrohalide) and a second step of using a base to liberate the amine again from the hydrohalide formed, wherein the base's hydrohalide formed in this double decomposition is liquid at up to 200° C. and therefore this salt phase can be separated off via simple liquid/liquid phase separation. In the process, a phase equilibrium becomes inevitably established depending on the solubilities of the components involved, and determines the composition of the two phases. To isolate the target product and achieve quantitative recovery of the amine, therefore, it is essential that these two components shall ideally not accumulate in the salt phase of the hydrohalide of the base, since this hydrohalide is typically disposed of or recycled. Particularly in the case of polar amines, however, accumulation in the salt phase is frequently observed, and so the salt phase has to be worked up at some cost and inconvenience to quantitatively recover the amines. For example, when primary amines are reacted with haloalkylsilanes to form the corresponding monosubstitution products, a substantially loss-free recovery of amine requires distillative removal of excess amine even before adding the base.

The object was to develop a method which no longer has the disadvantages of the prior art.

DESCRIPTION OF THE INVENTION

The invention relates to a method (I) for producing aminoorganyltriorganylsilanes of the general formula (1)

$$R'_{3-n}R^1{}_nSi-R^2-NR^3R^4 \quad (1),$$

by reacting cyclic or acyclic amines of the general formula (2), $$H-NR^3R^4 \quad (2)$$

with (haloorganyl)silanes of the general formula (3)

$$R'_{3-n}R^1{}_nSi-R^2-X \quad (3),$$

in which
R' is an acyloxy radical or an alkoxy radical having in each case 1-10 C atoms,
$R^1$ is a hydrocarbon radical having 1-10 C atoms,
$R^2$ is a divalent hydrocarbon radical having 1-10 C atoms,
$R^3$, $R^4$, independently of one another, are hydrogen or a hydrocarbon radicals having 1-10 C atoms, it also being possible for $R^3$, $R^4$ to be linked to one another and for the resulting cycle also to contain further heteroatoms, NH groups or $NR^{2a}$ groups, $R^{2a}$ is a divalent hydrocarbon radical having 1-10 C atoms,
n is a number equal to 0, 1, 2 or 3 and
X is chlorine, bromine or iodine,
the reaction comprising the successive steps:
a) reaction of 1.1 to 100 mol of the amine of the general formula (2) per mole of the (haloorganyl)silane of the general formula (3) at a temperature of from 0 to 250° C., the ammonium halide of the amine of the general formula (2) being formed as a byproduct in addition to the silane of the general formula (1),
b) addition of a base (B) to the reaction mixture, the base (B) containing at least 2 mol of basic functional groups per mole, double decomposition occurring in which the amine of the general formula (2) is liberated and base (B) is added in an amount such that at least 1.6 mol of the basic functional groups of the base (B) are present as hydrogen halide adduct,
c) distillation of the amine of the general formula (2) out of the reaction mixture,
d) addition of base (B) to the reaction mixture in an amount sufficient to form two liquid phases, one phase containing at least 90% by weight of the hydrohalide of the base (B), and
e) removal of the liquid phase which contains at least 90% by weight of the hydrohalide of the base (B).

The hydrocarbon radicals $R^1$, $R^2$, $R^{2a}$, $R^3$, $R^4$ may be saturated or unsaturated, branched or straight-chain, substituted or unsubstituted.

The hydrocarbon radicals $R^1$, $R^3$, $R^4$ may be alkyl radicals, such as the methyl, ethyl, n-propyl, isopropyl, 1-n-butyl, 2-n-butyl, isobutyl, tert-butyl, n-pentyl, isopentyl, neopentyl or tert-pentyl radical; hexyl radicals, such as the n-hexyl radical; heptyl radicals, such as the n-heptyl radical; octyl radicals, such as the n-octyl radical, and isooctyl radicals, such as the 2,2,4-trimethylpentyl radical; nonyl radicals, such as the n-nonyl radical; decyl radicals, such as the n-decyl radical; dodecyl radicals, such as the n-dodecyl radical; octadecyl radicals, such as the n-octadecyl radical; cycloalkyl radicals, such as the cyclopentyl, cyclohexyl or cycloheptyl radical and methylcyclohexyl radicals; alkenyl radicals, such as the vinyl, 1-propenyl and 2-propenyl radical; aryl radicals, such as the phenyl, naphthyl, anthryl and phenanthryl radical; alkaryl radicals, such as o-, m- and p-tolyl radicals; xylyl radicals and ethylphenyl radicals; and aralkyl radicals, such as the benzyl radical, the alpha- and the beta-phenylethyl radical; and combinations thereof linked by heteroatoms such as N, O, S, P. The hydrocarbon radicals $R^1$, $R^3$, $R^4$ preferably have 1-6, in particular 1-3, C atoms. Preferably, $R^1$ is the methyl, ethyl, isopropyl and n-propyl, isobutyl and n-butyl, pentyl, hexyl, heptyl, octyl, nonyl, decyl, phenyl, benzyl or allyl radical.

The radicals $R^3$ and $R^4$ are preferably selected from the preferred radicals of $R^1$ and furthermore from hydrogen or cyclohexyl or phenyl radicals. Preferably, not more than one of the radicals $R^3$ or $R^4$ is hydrogen. In a particularly preferred embodiment, the radical $R^3$ is a phenyl or cyclohexyl radical and the radical $R^4$ is hydrogen.

Furthermore, the radicals $R^3$ and $R^4$ may be linked directly or by heteroatoms so that, with the structural inclusion of the N atom, cyclic structures —$NR^3R^4$ result. Preferably, the cyclic structures —$NR^3R^4$ have 5 to 10 ring atoms, in particular 5, 6 or 8 ring atoms. Examples of these are the morpholino, piperidino or pyrrolidino radical, which are also preferred. Moreover, the radical —$NR^3R^4$ is preferably the N,N-bis(N',N'-dimethylaminopropyl) radical.

The radical R' preferably has the meaning of $OR^1$. Preferably, R' is a methoxy, ethoxy, isopropoxy and n-propoxy, butoxy, phenoxy, benzyloxy or allyloxy radical.

The radicals $R^2$ and $R^{2a}$ are preferably a divalent hydrocarbon radical having 1-6 C atoms, in particular a methylene, ethylene and propylene group, particularly preferably the methylene group.

The radical X is preferably chlorine or bromine, in particular chlorine.

n preferably has the value 1, 2 or 3.

Based on (haloorganyl)silane of the general formula (3), the amine of the general formula (2) is preferably used in excess, i.e. in molar ratios of preferably 1.5:1, particularly preferably of at least 2:1, especially preferably of at least 3:1 and preferably at most 50:1, more preferably at most 20:1 and even more preferably at most 10:1.

The invention furthermore relates to a method (II) for producing cyclic aminosilanes of the general formula (4)

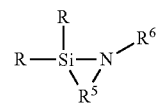  (4)

by reacting amines of the general formula (5),

with (haloorganyl)silanes of the general formula (6)

in which
$R^5$ is a divalent hydrocarbon radical having 1-10 C atoms in which the hydrocarbon chain may be interrupted by carbonyl groups, carboxyl groups, oxygen atoms, NH or $NR^8$ groups,
$R^6$ is hydrogen or a hydrocarbon radical having 1-10 C atoms which may be substituted by halogen atoms, OH groups and —$NH_2$, —$NHR^8$, $NR^8_2$ groups,
$R^7$ is hydrogen or a hydrocarbon radical having 1-10 C atoms which may be substituted by halogen atoms, OH groups and —$NH_2$, —$NHR^8$, $NR^8_2$ groups,
R is a hydrocarbon radical, an alkoxy radical having in each case 1-10 C atoms,
$R^8$ is a hydrocarbon radical having 1-10 C atoms, and
$Y^1$ and $Y^2$ are chlorine, bromine or iodine,
the reaction comprising the successive steps:
a) reaction of 1.1 to 1000 mol of the amine of the general formula (5) per mole of the (haloorganyl)silane of the general formula (6) at a temperature of from 0 to 300° C., the ammonium halide of the amine of the general formula (5) being formed as a byproduct in addition to the silane of the general formula (4),
b) addition of a base (B) to the reaction mixture, the base (B) containing at least 2 mol of basic functional groups per mole, double decomposition occurring, in which the amine of the general formula (5) is liberated and base (B) is added in an amount such that at least 1.6 mol of the basic functional groups of the base (B) are present as hydrogen halide adduct,
c) distillation of the amine of the general formula (5) out of the reaction mixture,
d) addition of base (B) to the reaction mixture in an amount sufficient to form two liquid phases, one phase containing at least 90% by weight of the hydrohalide of the base (B), and e) removal of the liquid phase which contains at least 90% by weight of the hydrohalide of the base (B).

$R^5$, $R^6$ and $R^7$ may be saturated or unsaturated, branched or straight-chain, substituted or unsubstituted.

Preferably, $R^5$ is a propylene or butylene group.

$R^6$ is preferably hydrogen or a cyclic or linear alkyl radical having 1-6 carbon atoms or a 3-aminopropyl radical. $R^7$ is preferably hydrogen or a cyclic or linear alkyl radical having 1-6 carbon atoms.

The examples and preferred radicals stated for R' and $R^1$ are also examples and preferred radicals for R.

The examples and preferred radicals stated for $R^1$ are also examples and preferred radicals for $R^8$.

The radicals $Y^1$ and $Y^2$ are preferably chlorine or bromine, in particular chlorine.

In a particularly preferred embodiment of the invention, the aminosilane of the general formula (5) is N-((3-aminopropyl)dimethylsilyl)-2,2-dimethyl-1-aza-2-silacyclopentane. In this case, the product in step a) is preferably formed from 2 molecules of chlorosilane in which $R^5$ is propylene, R is methyl and $Y^1$ and $Y^2$ are chlorine and 2 ammonia molecules, 4 molecules of ammonium chloride forming.

Based on the silane of the general formula (6), the amine of general formula (5) is preferably used at excess, i.e. in molar ratios of preferably at least 1.2:1, particularly preferably of at least 2:1 and especially preferably at least 3:1 and preferably at most 500:1, more preferably at most 100:1, in particular at most 10:1, especially preferably at most 6:1.

The invention further provides a method (III) for producing silylorganoamines of the general formula (7)

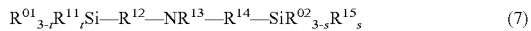
$$R^{01}{}_{3-t}R^{11}{}_t Si{-}R^{12}{-}NR^{13}{-}R^{14}{-}SiR^{02}{}_{3-s}R^{15}{}_s \qquad (7)$$

by reacting (aminoorganyl)silanes of the general formula (8),

$$H{-}NR^{13}{-}R^{14}{-}SiR^{02}{}_{3-s}R^{15}{}_s \qquad (8)$$

with (haloorganyl)silanes of the general formula (9)

$$R^{01}{}_{3-t}R^{11}{}_t Si{-}R^{12}{-}Z \qquad (9)$$

in which $R^{01}$ and $R^{02}$ are each an alkoxy radical having in each case 1-10 C atoms, $R^{11}$ and $R^{15}$ are each a hydrocarbon radical having 1-10 C atoms, $R^{12}$ is a divalent hydrocarbon radical having 1-10 C atoms wherein the hydrocarbon chain may be interrupted by carbonyl groups, carboxyl groups, oxygen atoms or sulfur atoms, $R^{14}$ is a divalent hydrocarbon radical having 1-10 C atoms wherein the hydrocarbon chain may be interrupted by carbonyl groups, carboxyl groups, oxygen atoms, sulfur atoms, NH or $NR^{18}$ groups, where $R^{18}$ has the same meaning as $R^{11}$, $R^{15}$.

$R^{13}$ is hydrogen, a hydrocarbon radical having 1-10 C atoms, or a radical of the general formula $R^{03}{}_{3-o}R^{16}{}_o Si{-}R^{17}{-}$ where
$R^{16}$ has the same meaning as $R^{11}$ and $R^{15}$,
$R^{17}$ has the same meaning as $R^{12}$ and $R^{14}$, and
$R^{03}$ has the same meaning as $R^{01}$ and $R^{02}$, and
s, t and o are each independently a number equal to 0, 1, 2 or 3, and Z is chlorine, bromine or iodine, the reaction comprising the successive steps:

a) reaction of 1.1 to 100 mol of the amine of the general formula (8) per mole of the (haloorganyl)-silane of the general formula (9) at a temperature of from 0 to 250° C., the ammonium halide of the amine of the general formula (8) being formed as a byproduct in addition to the silylorganoamine of the general formula (7), b) addition of a base (B) to the reaction mixture, the base (B) containing at least 2 mol of basic functional groups per mole, double decomposition occurring in which the amine of the general formula (8) is liberated and base (B) is added in an amount such that at least 1.6 mol of the basic functional groups of the base (B) are present as hydrogen halide adduct, c) distillation of the amine of the general formula (8) out of the reaction mixture, d) addition of base (B) to the reaction mixture in an amount sufficient to form two liquid phases, one phase containing at least 90% by weight of the hydrohalide of the base (B), and e) removal of the liquid phase which contains at least 90% by weight of the hydrohalide of the base (B).

The hydrocarbon radicals $R^{11}$, $R^{12}$, $R^{13}$, $R^{14}$, $R^{15}$, $R^{16}$, $R^{17}$ may be saturated or unsaturated, branched or straight-chain, substituted or unsubstituted.

The hydrocarbon radicals $R^{11}$, $R^{13}$, $R^{15}$, $R^{16}$ may be alkyl radicals, such as the methyl, ethyl, n-propyl, isopropyl, 1-n-butyl, 2-n-butyl, isobutyl, tert-butyl, n-pentyl, isopentyl, neopentyl or tert-pentyl radical; hexyl radicals, such as the n-hexyl radical; heptyl radicals, such as the n-heptyl radical; octyl radicals, such as the n-octyl radical, and isooctyl radicals, such as the 2,2,4-trimethylpentyl radical; nonyl radicals, such as the n-nonyl radical; decyl radicals, such as the n-decyl radical; dodecyl radicals, such as the n-dodecyl radical; octadecyl radicals, such as the n-octadecyl radical; cycloalkyl radicals, such as the cyclopentyl, cyclohexyl or cycloheptyl radical and methylcyclohexyl radicals; alkenyl radicals, such as the vinyl, 1-propenyl, 2-propenyl and the 10-undecenyl radical; aryl radicals, such as the phenyl, naphthyl, anthryl and phenanthryl radical; alkaryl radicals, such as o-, m- and p-tolyl radicals; xylyl radicals and ethylphenyl radicals; and aralkyl radicals, such as the benzyl radical, the alpha- and the beta-phenylethyl radical; and combinations thereof linked by heteroatoms such as N, O, S, P. The hydrocarbon radicals $R^{11}$, $R^{13}$, $R^{15}$, $R^{16}$ preferably have 1-6, in particular 1-3, C atoms. Preferably, $R^{11}$, $R^{15}$, $R^{16}$ are a methyl, ethyl, isopropyl and n-propyl, isobutyl and n-butyl, pentyl, hexyl, heptyl, octyl, nonyl, decyl, phenyl, benzyl or allyl radical.

The radical $R^{13}$ is preferably selected from the preferred radicals $R^{11}$, $R^{15}$, $R^{16}$ and furthermore from hydrogen or cyclohexyl or phenyl radicals or the radical of the general formula $R^{03}{}_{3-o}R^{16}{}_o Si{-}R^{17}{-}$. It is particularly preferable for the $R^{13}$ radical to be hydrogen.

The radicals $R^{01}$, $R^{02}$, $R^{03}$ preferably have the meaning of $OR^{11}$. Preferably $R^{01}$, $R^{02}$ and $R^{03}$ are each independently methoxy, ethoxy, iso- and n-propoxy, butoxy, phenoxy, benzyloxy or allyloxy. It is particularly preferable for the $R^{01}$, $R^{02}$ and $R^{03}$ radicals to be identical.

The radicals $R^{12}$, $R^{14}$ and $R^{17}$ are each preferably a divalent hydrocarbon radical having 1-6 C atoms, in particular a methylene, ethylene and propylene group and more preferably methylene and propylene.

The radical Z is preferably chlorine or bromine, in particular chlorine.

s, t and o each independently preferably has the value 0, 1 or 2 and more preferably 0 or 1.

Based on the silane of the general formula (9), the amine of the general formula (8) is preferably used at excess, i.e. in molar ratios of preferably at least 1.5:1, more preferably of at least 2:1 and especially of at least 3:1, and preferably at most 50:1, more preferably at most 20:1 and in particular at most 10:1.

In the presence of at least one radical $R^{01}$, $R^{02}$ or optionally $R^{03}$ in the silylorganoamine of the general formula (7) and when $R^{13}$ is hydrogen and at the same time at least one of the two radicals $R^{12}$ and $R^{14}$ consists of a carbon chain having at least 3 carbon atoms, there is a tendency especially at elevated temperatures and under reduced pressure, i.e. conditions of the type arising in a distillation for example, for the silylorganoamines to undergo an inter- or intramolecular displacement of an alkoxy radical by the NH group to form oligomers and cycles with Si—N linkage. Particularly the azasilacycles of the general formulae (10a) and (10b)

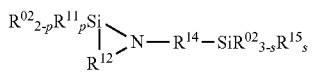  (10a)

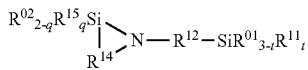  (10b)

formed from the silylorganoamine of the general formula (7) can accumulate, or even form quantitatively, in the distillate (p, q=0,1,2). However, the cyclic structure can be opened by adding the respective alcohol of the general formulae $R^{01}$—H, $R^{02}$—H or $R^{03}$—H to form the target product of the general formula (7). Typically, owing to the high reactivity of the Si—N bond, the addition of an alcohol quantity which is stoichiometric with regard to cycle is sufficient, and so any contamination of the silylorganoamine of the general formula (7) by an excess of alcohol can be avoided. Preferably, at least 1.0 mol and at most 1.1 mol and especially at most 1.05 mol of alcohol selected from $R^{01}$—H, $R^{02}$—H or $R^{03}$—H is added per mole of azasilacycles of the general formulae (10a) and (10b). To recover a general formula (7) target product free of or lean in azasilacycles it is also possible to add an excess of alcohol to the distilled reaction product and to distillatively remove the excess after completed reaction under more benign conditions than the distillation conditions of the target product of the general formula (7), so that recyclization is substantially avoided. The ring-opening reactions with alcohol of the azasilacycles formed from the target product of the general formula (7) typically proceed under mild conditions in a temperature range of at least 10° C., more particularly at least 15° C. and preferably at most 100° C., more particularly at most 50° C., the best reaction conditions are easily determined in an individual case by preliminary testing.

In the presence of at least one $R^{02}$ radical in the (aminoorganyl)silane of the general formula (8) and when the $R^{14}$ radical consists of a freely mobile chain of at least 3 atoms, there is a tendency particularly at elevated temperatures and under reduced pressure, i.e. conditions of the type arising in a distillation for example, for this (aminoorganyl)silane to undergo an inter- or intramolecular displacement of an alkoxy radical by the NH group to form oligomers and cycles with Si—N linkage. Especially the azasilacycle of the general formula (11)

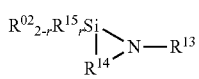  (11)

which is formed from the (aminoorganyl)silane of the general formula (8) can accumulate, or even form quantitatively, in the distillate (r=0,1,2).

However, the cyclic structure can be opened again by adding the particular alcohol $R^{02}$—H to form the (amino-organyl)silane of the general formula (8). Typically, owing to the high reactivity of the Si—N bond, the addition of an alcohol quantity which is stoichiometric with regard to the azasilacycle of the general formula (11) is sufficient, and so any contamination of the (aminoorganyl)silane by an excess of alcohol can be avoided. Preferably, at least 1.0 mol and at most 1.1 mol and especially at most 1.05 mol of alcohol $R^{02}$—H is added per mole of azasilacycles of the general formula (11). To recover a general formula (8) (aminoorganyl)silane free of or lean in azasilacycles it is also possible to add an excess of alcohol to the distilled starting material and to distillatively remove the excess after completed reaction under more benign conditions than the distillation conditions of azasilacycles of the general formula (11), and so recyclization is substantially avoided. The ring-opening reactions with alcohol of the azasilacycles of the general formula (11) generally proceed under mild conditions in the temperature range of at least 10° C., more particularly at least 15° C. and preferably at most 100° C. and more particularly at most 50° C., the best reaction conditions are easily determined in an individual case by preliminary testing.

In the processes (I), (II) and (III), the hydrohalide of base (B) is simple to separate as a liquid from the reaction mixture in a substantially loss-free manner.

The ammonium halide of the amine of the general formulae (2), (5) and (8) respectively is typically precipitated in step a) as an insoluble solid. In step c), the increasing depletion of the mixture in terms of amine of the general formulae (2), (5) and (8) respectively goes hand in hand with increasing formation of the hydrohalide of base (B), while, following very substantial distillative removal of the liberated amine, the chosen stoichiometry (ratio of employed (haloorganyl)silane of the general formulae (3), (6) and (9) respectively to base (B)) means that there are at least 1.6 mol and preferably at least 1.8 mol of the basic functional groups in base (B) per mole of base (B) present as hydrogen halide adduct. It is an essential property of the hydrogen halide adduct that under the distillation conditions of the amine of the general formulae (2), (5) and (8) respectively it does not decompose and remains in the distillation residue.

Provided more than one mole of basic functional groups in base (B) per mole of silane of the general formulae (3), (6) and (9) respectively were added in step b) and thus not all basic functional groups of base (B) are present as hydrogen halide adduct and base (B) is volatile under the distillation conditions of the amine of the general formulae (2), (5) and (8) respectively, a disproportionation reaction can take place during step c):

e.g. 2B*H-Hal→B↑+B*2H-Hal

In the course of this disproportionation reaction, the free basic functional groups present in base (B) increasingly convert into their hydrogen halide adducts and base (B) distills off until all the basic functional groups have been converted into their hydrohalides. With a view to optimizing the economics, the amount of base (B) added in step b) is preferably such that at most 25%, preferably at most 15%, more preferably at most 10% and even more preferably at most 2% of the basic functional groups in base (B) are not present as hydrogen halide adduct. Although some of the functional basic groups present in the added base (B) can already be present as hydrogen halide adduct. What is essential is merely that a sufficient number of free functional basic groups are available for the double decomposition of the hydrohalide of amine of the general formulae (2), (5) and (8).

Addition of further base (B) in step d) following the complete distillative removal of the amine of the general formulae (2), (5) and (8) reduces the ratio of hydrogen halide to base (B), and the melting point/viscosity of the resulting hydrohalide of base (B) decreases continuously with increasing amount of base (B) added. The hydrogen halide exchange typically takes place very rapidly, so that the effect of melting point lowering/viscosity decrease can already be tracked during the metered addition of base (B). Preferably, only sufficient base (B) is added here to completely liquefy the hydrohalide phase and lower its viscosity sufficiently to allow for its removal in step e). The amount of base (B) added in step d) is preferably at least 20% and more preferably at least 50% and preferably at most 200% and more preferably at most 150% of the amount of base (B) used in step b). The best conditions for the particular requirements are easily determined by a person skilled in the art by simple prior experimentation.

Preferably, the phase removed in step e) contains in step d) at least 95% by weight and more particularly at least 98% by weight of the hydrohalide of base (B).

A particular advantage of the process according to the present invention is the complete recovery of the amine of the general formulae (2), (5) and (8). By preferably fractional distillation in step c) it is possible to remove the amine from the other reaction partners such as base (B) and target product of the general formulae (1), (4) and (7) and other, secondary constituents, in a purity which permits re-use as a starting material for a subsequent batch.

In principle, the steps a) and b) can be effected in succession or simultaneously. Also conceivable is a time-lapsed procedure, beginning with step b), i.e. the addition of the base (B), that is to say after the beginning but still before the end of step a). If a base (B) which has free NH or $NH_2$ groups is used in the method according to the invention, step b), i.e. the addition of this oligoamine, is however preferably effected after the reaction in step a) is complete. Preferably used bases (B) are those which, in step b) of the method, form salts which form liquids at temperatures<150° C., particularly preferably <100° C. or <90° C. Particularly preferably used bases (B) are those which, in step d) of the method, form salts which form liquids at temperatures as low as <150° C., particularly preferably <100° C. or <90° C. An essential property of the bases (B) is forming (poly)hydrohalides which under the distillation conditions of the amine of the general formulae (2), (5) and (8) in step c) of the method and of the silane of the general formulae (1), (4) and (7) do not decompose and remain in the distillation residue.

Step a) of the method according to the invention is preferably carried out at temperatures of at least 50° C. In order to achieve a compromise between economically expedient reaction times and a reaction leading to as few byproducts as possible, temperatures of at least 80° C. and preferably at most 220° C., particularly preferably at most 150° C., have proven particularly advantageous.

Since step a) is generally exothermic, it is preferably carried out with cooling.

The steps b), c) and d) of the method according to the invention are independently of one another preferably carried out at temperatures of at least 0° C., particularly preferably of at least 20° C., in particular of 50° C. and preferably at most 250° C., particularly preferably at most 150° C., in particular at most 100° C. Preferably, the temperature remains constant during the steps b), c) and d) within a temperature frame of, preferably, 30° C., particularly preferably of 20° C. Since step b) is generally exothermic, it is preferably carried out with cooling. While steps a), b) and e) are preferably carried out under the pressure of the ambient atmosphere, the distillation of the amine of the general formulae (2), (5) and (8) is preferably carried out under reduced pressure in order that the thermal stress may be minimized and, where appropriate, the space-time yield will be increased by shortening the heating phase. Step d) is preferably carried out at atmospheric pressure or a pressure of 100 to 900 mbar and more preferably at a pressure at which the reaction mixture boils under reflux. This causes adhering salt above the level of liquid in the reaction vessel to be flushed away and makes it possible to avoid entraining ammonium halides into the aminoorganyltriorganylsilane of the general formulae (1), (4) and (7). All reaction steps are preferably carried out under inert gas, e.g. nitrogen and argon.

The method according to the invention may also have one or more of the following additional steps of the method:

a1) if the amine of the general formulae (2), (5) and (8) was used in excess in step a), this excess can be completely or partly separated off even before the addition of the base (B) in step b).

c1) The amine of the general formula (2), (5) or (8) may be further purified of other secondary constituents such as the base (B) by fractional distillation.

d) addition of one or more nonpolar solvents (L) to the product-containing phase. The additional solvent (L) can be added before, during or after the steps a), a1), b) and d) of the method. This measure preferably serves in steps a) and b) for reducing the viscosity of the mixture to ensure thorough mixing or flowability and preferably serves in step d) for reducing the solubility of the respective salt or salts in the organic phase. If the addition of the nonpolar solvent is effected after step d) of the method, the salts precipitated in this step are preferably separated off in an additional separation step, for example a filtration. The amounts of salt to be separated off are, however, small, and the removal is correspondingly simple. If the addition of the nonpolar solvent is effected before or during the step d), the respective salts are displaced from the product phase into the liquid phase, which substantially comprises the hydrohalide of the base (B), and are separated off together with said hydrohalide. Useful apolar solvents include linear and cyclic hydrocarbons, such as (cyclo)aliphatics, aromatics, and alkyl-aromatics such as paraffins, pentane, hexane, heptane, octane, decane, 10-undecene, isooctane, cyclohexene, decalin, cyclohexane, methylcyclohexane, benzene, toluene, o-xylene, m-xylene, p-xylene or mixtures thereof.

e) Fractional distillation or crystallization of the product phase isolated in step e) by phase separation can be used to further purify silane of the general formulae (1), (4) and (7). This is preferably employed for removing residual fractions of amine of the general formulae (2), (5) and (8), base (B) and/or optionally added apolar solvent (L), if these interfere with the use of products of the general formulae (1), (4) and (7).

It is possible for all components, in particular product of the general formulae (1), (4) and (7), amine of the general formulae (2), (5) and (8) and optionally the base (B) and the solvent (L), to be separated from one another by a single fractional distillation. This can also be effected by a plurality of separate distillation steps. Thus, for example, initially only the amine of the general formulae (2), (5) and (8) can be removed by distillation, the crude product initially remaining in the bottom product of the distillation and then being purified in a separate distillation or thin-film evaporation step.

f) Additional addition of ammonia to the product-containing phase after the phase separation in step e) and removal of the resulting ammonium halide. This measure can be suitable in particular for reducing the halide content in the end product.

g) Additional addition of alkali metal alcoholates, preferably sodium or potassium alcoholates, to the product-containing phase after the phase separation in step e) and removal of the resulting alkali metal halides. This measure may be suitable in particular for reducing the halide content in the end product.

h) Additional addition of polymeric polyamines to the product-containing phase after the phase separation in step e). This measure may serve for binding any residues of ionic halides so that these substantially remain behind in the bottom product of the distillation in a final distillation of the product of the general formulae (1), (4) and (7) and a correspondingly low-halide product is obtained.

i) Recovery or recycling of the amine of the general formulae (2), (5) and (8) which is optionally used in excess in step a) and of the amine of the general formulae (2), (5) and (8) which is liberated in step b). If the amine of the general formulae (2), (5) and (8) cannot be obtained, entirely or at least in parts, in sufficient purity by simple distillation—cf. step c)—the interfering products, byproducts or residues of the base (B) added in step b) can be separated off by one or more further purification steps. The following may be mentioned here by way of example further distillative purification steps of the amine fractions still not sufficiently pure after the first distillation (step c))

additional addition of aliphatic ketones or aldehydes to the product-containing phase after step e) or to the amine fractions distilled under step c). This measure can—if the base (B) added in step b) comprises compounds having primary amino groups—serve for converting residues of the base (B) still present in these phases into the corresponding imines. The latter can often be more easily separated off by distillation from the products and especially from the amines of the general formulae (2), (5) and (8) used in excess and/or liberated again in step b) than the base (B) itself.

l) Recovery of the base (B) used in step b), preferably by double decomposition of the resulting hydrohalide of this base with strong bases, e.g. alkali metal or alkaline earth metal hydroxides, carbonates, bicarbonates, alkoxides, etc. The respective bases can be used as such or in aqueous or nonaqueous solution or suspension. If aqueous solutions are used and/or water is liberated in the reaction, this is preferably separated off by distillation from the base (B). If ethylenediamine was used as base (B), this distillative separation is preferably effected at such high pressure that ethylenediamine and water no longer form an azeotrope.

If the base (B) is a compound, for example an amine, which is itself reactive toward the silane of the general formulae (3), (6) and (9), the amine of the general formulae (2), (5) and (8) is preferably purified by said steps of the method to such an extent that the content of the base (B) in the amines of the general formulae (2), (5) and (8) is below 3%, preferably below 1% and in particular below 0.5%.

In a particularly preferred combination of the described variants of the method according to the invention, the amine of the general formulae (2), (5) and (8) is used in excess with respect to the (halo-organyl)silane of the general formulae (3), (6) and (9). Addition of 0.5-0.8 mol equivalents of ethylene-diamine as base (B) with regard to (haloorganyl)silane (3), (6) or (9) in step b) causes a solid ethylene-diamine bishydrohalide to form and the amine of the general formula (2), (5) or (8) is completely liberated. Following distillative removal of the amine in step c), which preferably generates the amine in a purity such that it can be used again directly, the distillation residue in step d) is admixed with sufficient ethylenediamine as base (B) with respect to (haloorganyl)silane (3), (6) or (9) to form a second liquid phase of ethylenediamine hydrohalide, the halide content of which becomes established according to the ratio ethylenediamine/(haloorganyl)silane. The amount of ethylenediamine used is preferably at least 0.5 equivalent and at most 2, more preferably at most 1.5 and even more preferably at most 0.8 equivalents based on (haloorganyl)silane (3), (6) or (9). The salt phase is separated off (step e)) and the product phase is optionally purified by distillation.

Of course, the method can be carried out both batchwise, for example in stirred tanks, and continuously. The latter, for example, by effecting steps a), b) and optionally further steps (see above) in a tubular reactor or a stirred vessel cascade. The individual substances are metered in or mixed in together or—preferably—in succession. Suitable methods, for example with the use of settling vessels, decanters, etc., are known and are widely described in the literature also for the subsequent continuous phase separation (step e).

Preferably, the water content of the amines of the general formulae (2), (5) and (8) which are to be used is from 0 to 20 000 ppm, preferably from 0 to 5000 ppm, particularly preferably from 0 to 1000 ppm.

The $pK_b$ value of the amines of the general formulae (2), (5) and (8) which are to be used is preferably greater than that of the base (B), preferably at least 1 $pK_b$ unit greater, particularly preferably 2 $pK_b$ units greater.

In a preferred embodiment, compounds whose boiling point differs both from the product (1), (4) or (7) and from the amine of the general formulae (2), (5) and (8) by at least 40° C., preferably by at least 60° C. and particularly preferably at least 90° C. are chosen as base (B), so that residues of base (B) which remain in the organic phase in the phase separation in step e) can be separated off sufficiently well by distillation both from the product of the general formulae (1), (4) and (7) and from the amine of the general formulae (2), (5) and (8).

Oligoamines (O) containing ethylene- or propylenediamine units or mixtures thereof are preferably used as base (B). Preferably, the oligoamines (O) contain from 1 to 20, in particular from 1 to 10, ethylene- or propylenediamine units. Preferred oligoamines (O) are ethylenediamine, diethylentriamine, triethylenetetramine, tetra-ethylenepentamine, diazabicyclooctane, pentamethyl-diethylenetriamine, 1,2-propylenediamine, 2,2-dimethyl-propane-1,3-diamine, 1,2-dimethylimidazole, N-methyl-imidazole, N4-amine (from BASF SE, Germany).

Ethylenediamine is particularly preferably used as base (B). Thus, ethylenediamine shows the following surprising combination of properties in the method according to the invention:

The addition of ethylenediamine leads in step b) to substantially complete double decomposition even when only the particularly preferred amount of ethylenediamine of from 0.5-0.8 equivalents, based on the amount of the (haloorganyl)silane of the general formulae (3), (6) and (9), is added.

In the course of the formation of the ethylene-diamine bishydrohalide in step b), in particular in the case of aniline derivatives, the thermal stability is increased considerably, which is of great advantage with respect to the thermal reaction safety. Evidently the formation of thermally unstable anilinium salts (ammonium compounds of the silanes of the general formula (1), (4) and (7)) thereby shifts to higher temperatures.

The solid phase of bishydrohalide formed in step b) can simply be liquefied by further addition of ethylenediamine (the salt phase obtained in step d) has a melting point of about 80° C.)

The liquid salt phase separates completely from the organic phase after only a few minutes and can therefore be separated off without a large and hence expensive time requirement for a phase separation.

With the method according to the invention, aminoorganyltriorganylsilanes of the general formula (1), cyclic aminosilanes of the general formula (4) and aminoorganylsilanes of the general formula (7) can be obtained in a simple manner in good to very good yields. The methods can be implemented on an industrial scale easily and without danger.

The purity of the aminoorganyltriorganylsilanes of the general formula (1), the cyclic aminosilanes of the general formula (4) and the aminoorganylsilanes of the general formula (7) which are produced according to the invention is preferably at least 85%, particularly preferably at least 90%. This purity can be increased to more than 90% by means of an optional downstream distillation step e) of the product.

Compared with the prior art, the method according to the invention has the advantage that the main proportion of the ammonium salts of the amines of the general formulae (2), (5) and (8), which salts form as byproduct, need no longer be separated off as solid, which is generally complicated and expensive on the industrial scale, in particular in the case of poorly crystallizing ammonium salts (for example the ammonium salts of aniline). As a result of the double decomposition, two liquid phases can now be separated from one another in a simple manner. Moreover, wash steps of the filter cake with solvent additionally to be used are unnecessary. At the same time, the formation of byproducts can be significantly reduced by the use of optimized excesses of amine according to the general formulae (2), (5) and (8). Moreover, it is remarkable that the method according to the invention is suitable for recovering the often comparatively expensive amines of the formulae (2), (5) and (8) which would be consumed in step a) for the formation of the corresponding ammonium salts, by the double decomposition with the generally relatively economical base (B), e.g. ethylenediamine, and thereby making said amines accessible for reuse. The resulting hydrohalides of the base (B) can if necessary likewise be recovered again by known methods so that besides neutralization water only harmless salts such as sodium chloride (common salt), for example, are generated as byproducts of the overall process.

All above symbols of the above formulae have their meanings in each case independently of one another. In all formulae, the silicon atom is tetravalent.

In the following examples, unless stated otherwise in each case, all stated amounts and stated percentages are based on weight, all pressures 0.10 MPa (abs.) and all temperatures 20° C.

EXAMPLE 1

Production of
4-(triethoxysilylmethyl)tetrahydro-1,4-oxazine 305 g of dry morpholine ($pK_b$ 5.67) were heated to reflux (127° C.) in a 1000 ml four-necked flask having a reflux condenser, KPG stirrer and thermometer and 305.8 g of chloromethyltriethoxysilane were added in the course of 60 min with stirring. During the metering reflux was maintained. In the process, the temperature increased successively to 153° C. After the end of the addition, stirring was continued for 15 min at this temperature. 46.3 g of ethylenediamine ($pK_b$ 4.07) were added to the mixture in the course of 15 min with stirring, solid ethylenediamine bishydrochloride precipitating. The pale beige suspension was stirred under reflux (137° C.) for 60 min. Thereafter, low boilers were distilled off at up to 94° C./5 hPa to obtain 193.9 g of a colorless, clear fraction which, according to GC, contained 90% of morpholine, 5.2% of ethanol, 2.45% of 4-(triethoxysilylmethyl)tetrahydro-1,4-oxazine and 1.5% of ethylenediamine. Accordingly, 95% of the morpholine were recovered. The distillation residue was admixed with 120 g of ethylenediamine at 50° C. by stirring for 15 min. Following addition of 50 g of cyclohexane, two liquid phases formed. The lower, ethylenediamine hydrochloride phase was drained off. The upper phase was distilled at up to 92° C./5 hPa to remove low boilers and obtain 61.4 g of a colorless, clear fraction which, according to GC, contained 78.6% of cyclohexane, 16% of ethanol and 4.6% of morpholine. The residue was filtered to isolate 330.3 g of clear yellowish filtrate which, according to GC, contained 90% of 4-(triethoxy-silylmethyl)tetrahydro-1,4-oxazine. Fractional distillation gave 289 g of a colorless, clear fraction containing 98% of 4-(triethoxysilylmethyl)tetrahydro-1,4-oxazine (yield 77%).

EXAMPLE 2

Production of
N-phenylaminomethyltrimethoxysilane

In a 500 ml four-necked flask having a reflux condenser, KPG stirrer and thermometer, 163.7 g of dry aniline ($pK_b$ 9.4) were heated to 100° C. and 60 g of chloromethyltriethoxysilane were added in the course of 180 min with stirring and stirring was effected for a further 60 min. Thereafter, 11.6 g of ethylenediamine ($pK_b$ 4.07) were added to the mixture in the course of 10 min with stirring, a white precipitate of ethylenediamine bishydrochloride precipitating. At constant temperature (100° C.), stirring was effected for a further 60 min. Subsequently, a vacuum was applied and 124 g of aniline (GC purity 98.5%; yield 95%) distilled at 85° C. and 10 hPa. At 100° C., the distillation residue was admixed with 13.7 g of ethylenediamine. In the process, a liquid phase of ethylenediamine hydrochloride formed and was separated off at 80° C. The upper phase was subjected to fractional distillation via a Vigreux column. With a boiling point of 137° C. at 10 pHa, 59.6 g (yield 72%) of N-phenylaminomethyl-trimethoxysilane were obtained, the purity of which was determined as 96.6%.

EXAMPLE 3

Production of
N-phenylaminomethyldimethoxymethylsilane

In a 2000 ml five-necked flask having a reflux condenser, KPG stirrer and thermometer, 1413 g of dry aniline ($pK_b$ 9.4) were heated to 100° C. and 450 g of (chloromethyl)dimethoxysilane were added in the course of 180 min with stirring and stirring was effected for a further 60 min. Thereafter, 96.2 g of ethylenediamine ($pK_b$ 4.07) were added to the mixture in the course of 10 min with stirring, a precipitate of ethylenediamine bishydrochloride being formed. At constant temperature (100° C.), stirring was effected for a further 60 min.*) Vacuum was then applied to obtain a distillate at up to 110° C. at 20 hPa 1141 g of aniline (GC purity 95.3%+2% of N-phenylaminomethyldimethoxymethylsilane; aniline yield 100%). The distillation residue was admixed with 113.6 g of ethylenediamine at 100° C. and a pressure of 85 hPa in the course of 4 minutes. The resulting weak reflux caused deposits which had formed in the vapor space of the apparatus to become rinsed off. In the process, a liquid phase of ethylenediamine hydrochloride formed and was separated off at 80° C. The upper phase was heated to 115° C. at 10 hPa. The residue left behind was a mixture of 88.1% of phenylaminomethyldimethoxymethylsilane, 4.8% of bis[(dimethoxymethylsilyl)methyl]amine, 2.9% of 1,3-bis(N-phenylaminomethyl)-1,3-dimethoxy-1,3-dimethyldisiloxane. The yield of target product was 86%.

*) The reaction mixture was subjected to a DSC measurement and showed an exothermic decomposition from 310° C. (<−450 kJ/kg, after distillative removal of aniline: −883 kJ/kg).

EXAMPLE 3a

Not According to the Invention

In a comparative test, following the reaction of (chloromethyl)dimethoxymethylsilane with aniline under reaction conditions analogous to Example 3, the aniline excess was distilled off without the prior addition of ethylenediamine. A DSC measurement of the reaction mixture showed an exothermic decomposition from 197° C. (−1025 kJ/kg). After distillative removal of the aniline, the decomposition temperature had come down to 168° C., and the decomposition enthalpy was <−1312 kJ/kg. The decomposition enthalpy of −1312 kJ/kg corresponds to an adiabatic temperature increase of about 875° C. Under a prolonged thermal stress of the type customary with distillation operations, a progressive decrease in decomposition temperature (onset temperature) can occur. This means that if no ethylenediamine is added in the above-mentioned process, i.e. without the conversion of aniline hydrochloride into ethylenediamine bishydrochloride, a high safety risk is incurred.

EXAMPLE 4

Production of bis((3-trimethoxysilyl)propyl)amine

In a 4000 ml five-necked flask equipped with reflux condenser, KPG stirrer, thermometer and 30 cm Vigreux column, 1906.8 g of 3-aminopropyltrimethoxysilane (Geniosil® GF 96, commercially available from Wacker Chemie AG, Germany) were initially charged at 130° C. and admixed with 696.3 g of 3-chloropropyltrimethoxysilane in the course of 120 min by stirring. On completion of the addition the mixture was subsequently stirred at this temperature for 240 min. The mixture was cooled down to 110° C. and admixed with 115.8 g of ethylene-diamine in the course of 3 min by stirring to form a solid ethylenediamine bishydrochloride precipitate. This was followed by distillation through a Vigreux column. Up to 105° C./10 hPa 1318.8 g of a colorless, clear low-boiler fraction containing, according to GC, 87.4% of 3-aminopropyltrimethoxysilane, 1% of methanol and 7.9% of ethylenediamine passed over. An intermediate cut was taken off at up to 135° C./10 hPa and found by GC to contain 74% of 3-amino-propyltrimethoxysilane, 8.3% of bis((3-trimethoxysilyl)propyl)amine, 11.8% of the cyclization product (=1,1-dimethoxy-1-sila-2-(3-(trimethoxysilyl)propyl)aza-cyclopentane) and 1.4% of ethylenediamine. The cold trap collected 27.6 g of a 1:1 mixture of methanol and ethylenediamine. Accordingly, the 3-aminopropylsilane was recovered quantitatively. 305.4 g of ethylene-diamine were added to the distillation residue at 100° C. to form a liquid lower phase which was drained off at 80° C. The upper phase was heated up and the distillation residue filtered to obtain 981 g of a mixture of 85% of bis((3-trimethoxysilyl)propyl)amine, 1.4% of the cyclization product (=1,1-dimethoxy-1-sila-2-(3-(trimethoxysilyl)propyl)azacyclopentane), 7.4% of tris((3-trimethoxysilyl)propyl)amine and 1.7% of 3-aminopropyltrimethoxysilane.

The invention claimed is:

1. A method (I) for producing an aminoorganyltriorganylsilane of the general formula (1)

by reacting a cyclic or acyclic amine of the general formula (2),

with a (haloorganyl)silane of the general formula (3)

in which
R' is an acyloxy radical or an alkoxy radical having in each case 1-10 C atoms,
$R^1$ is a hydrocarbon radical having 1-10 C atoms,
$R^2$ is a divalent hydrocarbon radical having 1-10 C atoms,
$R^3$, $R^4$, independently of one another, are hydrogen or a hydrocarbon radical having 1-10 C atoms, it also being possible for $R^3$, $R^4$ to be linked to one another and for a resulting cycle also to contain further heteroatoms, NH groups or $NR^{2a}$ groups,
$R^{2a}$ is a divalent hydrocarbon radical having 1-10 C atoms,
n is a number equal to 0, 1, 2 or 3 and
X is chlorine, bromine or iodine, the reacting comprising the successive steps:
a) reaction of 1.1 to 100 mol of the amine of the general formula (2) per mole of the (haloorganyl)silane of the general formula (3) in a reaction mixture at a temperature of from 0 to 250° C., an ammonium halide of the amine of the general formula (2) being formed as a byproduct in addition to the silane of the general formula (1),
b) addition of a base (B) to the reaction mixture, wherein the base (B):
  (1) is an oligomine (O) containing ethylene-or propylenediamine units or mixtures thereof;
  (2) the boiling point of base (B) differs by at least 40° C. from a boiling point of the aminoorganyltriorganylsilane (1) as well as from a boiling point of the amine of the general formula (2);and
  (3) the base (B) contains at least 2 mol of basic functional groups per mole; wherein on the addition of base (B), double decomposition occurs in which the amine of the general formula (2) is liberated and base (B) is added in an amount such that at least 1.6 mol of the basic functional groups of the base (B) are present as hydrogen halide adduct,
c) distillation of the amine of the general formula (2) out of the reaction mixture,
d) addition of base (B) to the reaction mixture in an amount sufficient to form two liquid phases, one phase containing at least 90% by weight of a hydrohalide of the base (B) and
e) removal of the liquid phase which contains at least 90% by weight of the hydrohalide of the base (B).

2. The method as claimed in claim 1, in which the amount of base (B) added in step d) is from 20 to 200% of the amount of base (B) used in step b).

3. The method as claimed in claim 1, in which steps b), c) and d) are carried out at temperatures of 20° C. to 250° C.

4. The method as claimed in claim 1, in which a water content of the amine of the general formula (2) which is to be used is in a range from 0 to 20000 ppm.

5. The method as claimed in claim 1, in which a $pK_b$ value of the amine of the general formula (2) which is to be used is at least 1 $pK_b$ unit greater than a $pK_b$ value of base (B).

6. The method as claimed in claim 1, in which the base (B) is a member selected from the group consisting of ethylenediamine, diethylenetriamine, triethylenetetramine, tetraethylenepentamine, diazabicyclooctane, pentamethyldiethylenetriamine, 1,2-propylenediamine, 2,2-dimethylpropane-1,3-diamine, 1,2-dimethylimidazole, N-methylimidazole and mixtures thereof.

* * * * *